US006663387B2

United States Patent
Riley

(10) Patent No.: US 6,663,387 B2
(45) Date of Patent: Dec. 16, 2003

(54) NEAR NET TOOTH SHAPED CERAMIC CROWN AND METHOD

(75) Inventor: Robert Riley, Vista, CA (US)

(73) Assignee: Centerpulse Dental Inc., Carlsbad, CA (US)

(*) Notice: Subject to any disclaimer, the term of this patent is extended or adjusted under 35 U.S.C. 154(b) by 0 days.

(21) Appl. No.: 09/855,136

(22) Filed: May 14, 2001

(65) Prior Publication Data

US 2002/0168614 A1 Nov. 14, 2002

(51) Int. Cl.[7] ................................ A61C 8/00
(52) U.S. Cl. ...................... 433/173; 433/218
(58) Field of Search ................ 433/218, 172, 433/175, 173, 201.1

(56) References Cited

U.S. PATENT DOCUMENTS

| | | | |
|---|---|---|---|
| 4,547,157 A | 10/1985 | Driskell | 433/173 |
| 4,872,840 A | 10/1989 | Bori | 433/173 |
| 5,080,589 A | * 1/1992 | Oden et al. | 433/202.1 |
| 5,180,303 A | * 1/1993 | Hornburg et al. | 433/173 |
| 5,312,254 A | 5/1994 | Rosenlicht | 433/173 |
| 5,350,302 A | * 9/1994 | Marlin | 433/173 |
| 5,447,435 A | * 9/1995 | Brodbeck | 433/172 |
| 5,571,016 A | 11/1996 | Ingber et al. | 433/173 |
| 5,584,693 A | 12/1996 | Nishihara | 433/169 |
| 5,620,323 A | * 4/1997 | Bressman et al. | 433/174 |
| 5,674,069 A | 10/1997 | Osorio | 433/172 |
| 5,685,714 A | 11/1997 | Beaty et al. | 433/172 |
| 5,785,524 A | 7/1998 | Wolf | 433/173 |
| 5,833,463 A | 11/1998 | Hurson | 433/173 |
| 5,899,695 A | 5/1999 | Lazzara et al. | 433/173 |
| 5,934,906 A | 8/1999 | Phimmasone | 433/172 |
| 5,947,732 A | 9/1999 | Beaty et al. | 433/172 |
| 5,989,026 A | 11/1999 | Rogers et al. | 433/172 |
| 6,012,923 A | 1/2000 | Bassett et al. | 433/172 |
| 6,039,568 A | 3/2000 | Hinds | 433/175 |
| 6,045,361 A | 4/2000 | Misch et al. | 433/214 |
| 6,048,203 A | 4/2000 | Rosenberg | 433/173 |
| 6,126,445 A | 10/2000 | Willoughby | 433/223 |

* cited by examiner

*Primary Examiner*—Kevin Shaver
*Assistant Examiner*—Melba Bumgarner
(74) *Attorney, Agent, or Firm*—Kenneth S. Barrow

(57) ABSTRACT

A near net tooth shaped ceramic prosthesis is provided in a tooth shape to minimize the amount of cutting and baking required to finish the outer crown portion of the dental prosthesis. A metallic core is provided for attachment to an implant in a patient's mouth. A ceramic crown is then attached to the core.

17 Claims, 7 Drawing Sheets

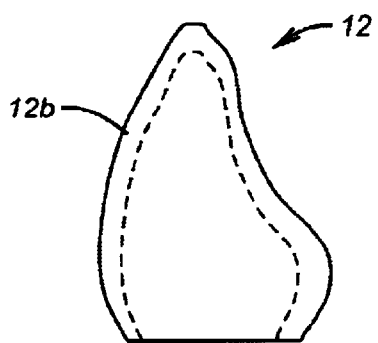
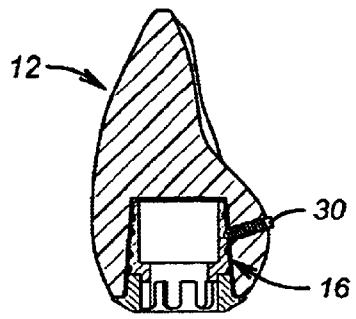
FIG. 6  FIG. 8
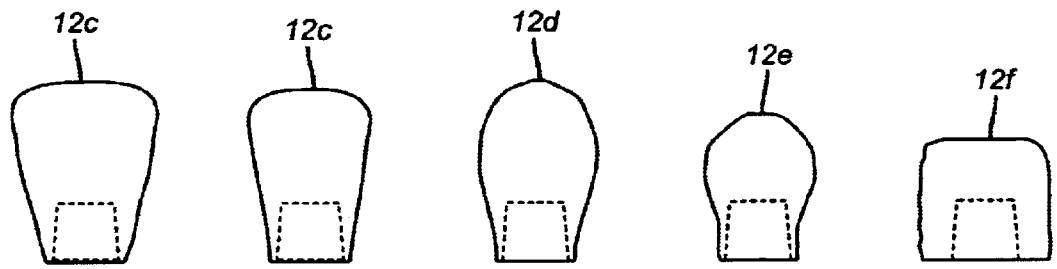
FIG. 7a  FIG. 7b  FIG. 7c  FIG. 7d  FIG. 7e

NEAR NET TOOTH SHAPED CERAMIC CROWN AND METHOD

BACKGROUND

This disclosure relates to prefabricated ceramic crowns supported on dental implants.

One shortcoming of conventional dental implant restorations is that metal abutments can disrupt the translucence of the porcelain used to fabricate the crown. Dental abutments are typically made from titanium or other biocompatible metals. These metals are most often metallic gray in color and hence can have aesthetic disadvantages in dental restorations. In some instances, the abutment can be visible through the gingival tissue and present a grayish color in the transgingival region of the patient. Visibility of the abutment is greatly undesired, especially in the anterior region of the mouth where aesthetics have a crucial importance. In other instances, the tissue and bone surrounding the coronal end of the implant can recede. A portion of the abutment can be exposed and reveal a grayish color in the mouth of the patient.

Conventional dental implant restorations have other shortcomings as well. For example, much time and effort are needed to shape ceramic crowns to have a natural tooth-like configuration. Ceramic crowns currently on the market require the dental laboratory either to add or remove a substantial amount of material to the crowns to bring them to the approximate shape of a tooth. Material is added by baking porcelain to the ceramic surface. Many times, multiple layers of porcelain need to be added to achieve a natural shape and color. Each layer must be baked onto the crown before the next layer can be added. Multiple baking cycles can adversely affect the underlying ceramic substrate.

As another disadvantage, it is difficult to remove material from a hardened ceramic crown; and ceramics typically are very difficult to cut due to their hardness. Special water cooled diamond tools need to be used for such cuts. The stress associated with cutting the crown can also create microscopic fractures in the ceramic that weaken the material and make it susceptible to fatigue and ultimately failure.

Ceramic crowns are sold with various geometric shapes. One dental company sells crowns with a cone-shaped ceramic cylinder having an internal metal core. The ceramic cylinder tapers outwardly from the coronal end of the implant. The metal core is designed with a hexagon or other anti-rotational shape that is selected to match a mating feature on the implant body. Typically, the ceramic cylinder is large enough so excess material can be cut away to shape the crown. If the crown is not large enough, multiple layers of porcelain are baked to the outer surface to form the desired shape.

Other dental companies sell ceramic crowns with a generally cylindrical shape. The cylinder is sized slightly larger than the implant to facilitate cutting the crown to the geometry of a natural tooth. At the apical end of the crown, the ceramic tapers inwardly to the implant diameter. The cylinders include an anti-rotational feature to engage a coronal end of the implant.

Still, other companies manufacture ceramic caps that are cement-retained to a metal abutment. The ceramic cap has a cylindrical shape and must be cut to the shape and size of a natural tooth.

In light of prior ceramic prosthetic teeth and abutments, a ceramic crown that is initially shaped like a tooth would have many advantages over the prior art. The present invention provides such an advantage and other advantages taught herein.

SUMMARY

The present invention is directed toward a prosthetic tooth that is manufactured to have a shape and size of a natural human tooth. The prosthetic tooth has an internal metallic core and an external ceramic crown. The core generally has a cylindrical configuration, an internal bore, and one end adapted to connect to a dental implant. The crown is formed from a ceramic that surrounds the outer surface of the core. Most importantly, the crown is manufactured to have an anatomical shape and size of a natural human tooth, such as incisors, molars, premolars, or canines. During a dental restoration, the clinician or laboratory chooses a correctly shaped and sized crown according to the tooth or teeth being restored.

A principal advantage of the present invention is the crown has a shape that closely resembles the shape of a natural tooth. This near net tooth shape of the crown will reduce the amount of work, time, and expense required to create a final dental prosthetic restoration. Further, the ceramic used to fabricate this crown is compatible with commercially available porcelains so that the gradients of shade and translucence of the natural tooth can be replicated. Also, the crown may be manufactured to have a size that is slightly smaller than the average natural tooth. This difference in size enables the crown to receive an additional layer of porcelain and then match the exact size of the natural tooth.

As another advantage, the prosthetic teeth of the present invention may be manufactured and sold as a kit. Each kit would include a plurality of prosthetic teeth having different sizes and shapes emulating different sizes and shapes of natural human teeth. A clinician could chose a prosthetic tooth to best match particular needs of a patient.

The present invention could also be manufactured and sold as a dental implant prosthetic system. This system would include both a dental implant and prosthetic tooth of the present invention.

BRIEF DESCRIPTION OF THE DRAWINGS

FIG. 6 is a side-view illustrating an embodiment of a near net tooth shaped crown.

FIGS. 7a–7e are views illustrating a plurality of tooth shapes for the near net tooth shaped crown.

FIG. 8 is a cross-sectional side view illustrating an embodiment of a threaded attachment of a near net tooth shaped crown and a core member.

DETAILED DESCRIPTION

Figure 1:
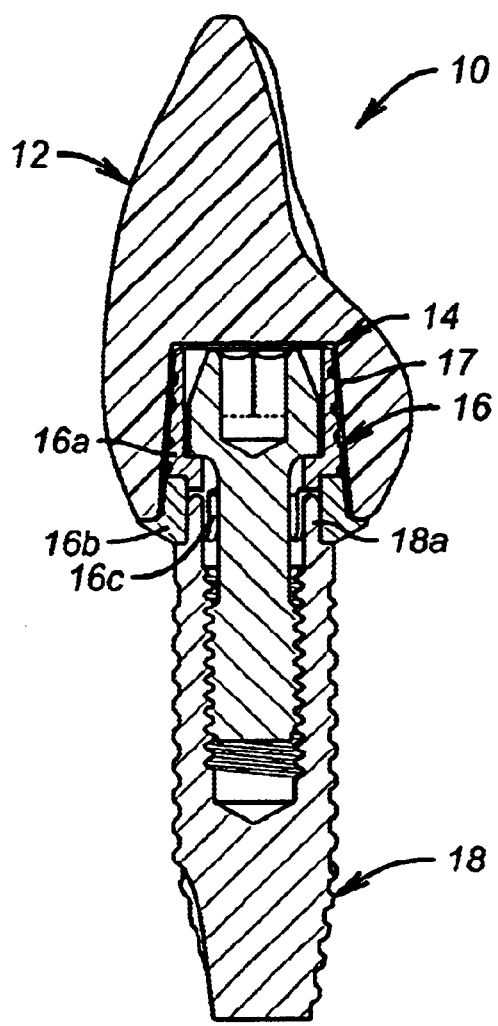
FIG. 1 is a cross-sectional side view illustrating an embodiment of a dental prosthetic assembly according to one embodiment of the invention.

A dental prosthetic assembly is generally designated 10 in FIG. 1 and includes a tooth-like prosthesis having a near net tooth shaped crown 12 and a metallic core 16. The crown 12 has an internal bore 14 to receive the core and is manufactured to have a size and shape of a natural human tooth.

The core 16 is connected to a jawbone anchor or dental implant 18. This anchor 18 may be any one of various dental implants known to those skilled in the art, such as an externally threaded Spline implant, Spline cylinder implant, or an externally threaded implant or cylinder implant with an internal hexagonal connection; these implants are manufactured by Sulzer Dental Inc. of California.

Figure 2:
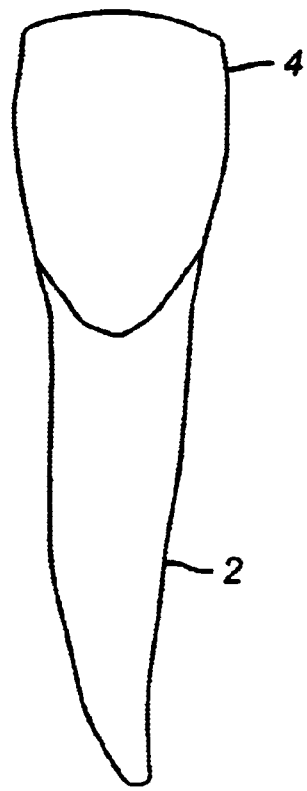
FIG. 2 is a front view of a natural human tooth.

FIG. 2 shows a natural human tooth with a root portion 2 and a natural crown portion 4. The crown 12 of FIG. 1 emulates the natural crown 4 of FIG. 2 and not the root portion 2 of the natural tooth.

Figure 3:
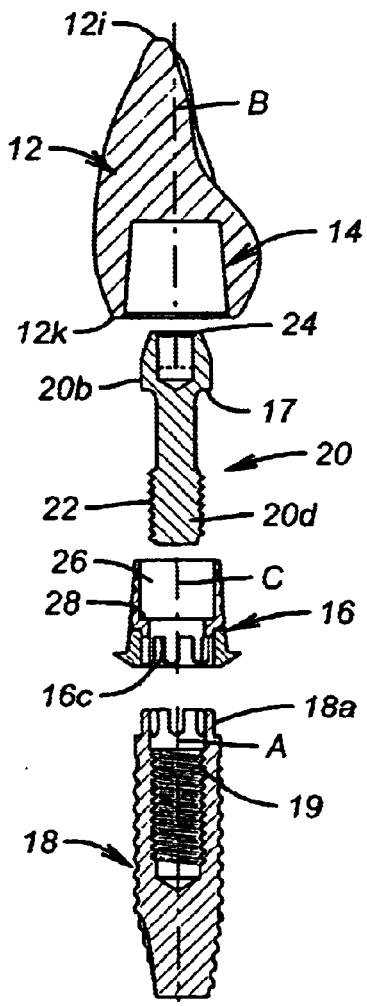
FIG. 3 is an exploded cross-sectional side view illustrating an embodiment of a dental prosthetic assembly.

Looking to FIGS. 1 and 3, a threaded fastener or screw 20 may be used to connect the core 16 to the anchor 18. The fastener includes a first end 20a having threads 22 and a second end 20b having a polygonal socket 24. A tool (not shown) can be inserted into socket 24 to turn fastener 20 into threaded engagement with a threaded bore 19 in anchor 18. Core 16 includes a screw bore 26 and a screw seat 28.

Screw bore 26 includes an axis C that extends substantially co-axially with an axis A of anchor 18. Fastener 20 is inserted through core 16 and threaded into anchor 18. When fully seated, a shoulder 17 of second end 20b of threaded fastener 20 is seated on screw seat 28 within core 16. Further, an axis B passes through the near net crown 12 from an incisal edge 12i to a cervix 12k. In FIG. 3, all axes (A, B, and C) are longitudinal and co-axial.

Figure 4:
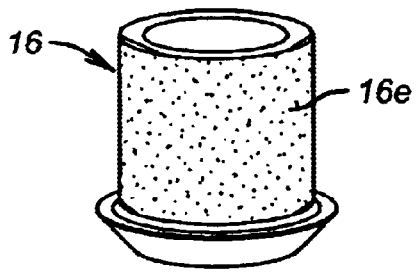
FIG. 4 is a perspective view illustrating an embodiment of a core member.

The core 16 is preferably formed of a material selected for fatigue strength suitability such as a metal, like titanium or titanium alloy. The metal core can be fabricated with various shapes, such as a cylindrical geometry (shown in FIG. 4) or a frusto-conical geometry (shown in FIG. 5). Further, the core may be formed from one piece (as shown in FIG. 4, for example) or formed from two or more pieces. FIG. 1 shows a core formed from two pieces: a core body 16a and a core cuff 16b.

Preferably, the core anti-rotationally engages the implant. The anti-rotational engagement between the core and implant may occur with numerous techniques known to those skilled in the art. Some examples of these techniques include male and female polygonal projections or locking tapers. FIGS. 1 and 3 show a spline connection between the core and implant. In this connection, a plurality of splines 16c on the core engage a plurality of mating splines 18a on anchor 18.

Figure 5:
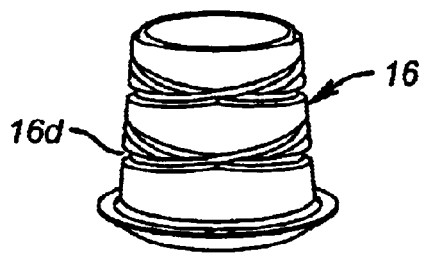
FIG. 5 is a perspective view illustrating another embodiment of a core member.

The outer surface of the core may have various textures, coatings, and configurations. FIG. 4, for example, shows core 16 with a textured coating 16e on the outer surface. FIG. 5 shows core 16 having a plurality of grooves 16d. The various textures and coatings can enhance the strength of connection between the core and crown.

While ceramics can be strong, they are often brittle. The addition of a metallic core adds strength to the overall assembly. This added strength is especially important at the implant interface where forces are transferred from the restoration to the anchoring implant.

Crown 12, FIG. 6, is formed of an aesthetic suitable material, such as a ceramic material, an unfired ceramic material, a polymer material, or a combination of ceramic and polymer materials. Preferably, the crown is made from a ceramic, such as aluminum oxide, zirconium oxide, or a composite thereof. These materials can be made to have mechanical strength sufficient to support occlusal forces and are relatively inert when exposed to body fluid and tissues. These materials also allow for the addition of porcelain to their surface to provide shading to the unique color of the adjacent natural dentition. A clinician, laboratory, or the like may add a layer of porcelain to the outer surface of the crown to match the aesthetics of adjacent natural teeth. The crown can also be manufactured and sold with a thin layer of porcelain 12b already applied to its surface. This latter application facilitates minor modifications to the final prosthetic restoration.

In one embodiment, the crown may be manufactured to have a size that is slightly smaller than the average natural tooth. For example, the crown can be manufactured to have an outside surface or outside diameter that is 0.5 mm to 1.5 mm smaller than the natural tooth to be replaced. This difference in size enables the crown to receive an additional layer of porcelain and then match the exact size of the natural tooth.

One important advantage of the present invention is that the crown is manufactured to have shapes approximately equal to the natural shapes of human dentition. The crowns, manufactured in these shapes are thus prefabricated and sold to clinicians, laboratories, and the like in the shape of human teeth. Since ceramic materials are typically difficult to shape using machining techniques, the present invention significantly reduces or completely eliminates the amount of machining required to create the shape and size of the final prosthetic restoration.

Crown 12 may be provided in a kit to have a plurality of different sizes and shapes that mimic the sizes and shapes of natural human teeth. These shapes, for example, could include tooth shapes such as an incisor 12c, FIGS. 7a, 7b, a canine 12d, FIG. 7c, a premolar 12e, FIG. 7d and a molar 12f, FIG. 7e. Crown 12 may be attached to core 16 by various means known to those skilled in the art. In FIG. 1, the bore 14 in the ceramic crown 12 is made slightly larger that the outside diameter of the core 16. This difference in size creates a cement gap 17. The cement gap is a space for dental cement that holds the crown to the core. In FIG. 7, an alternative connecting method is shown, a threaded fastener 30, such as a set screw, is used to attach crown 12 to core 16.

Figures 9, 10:
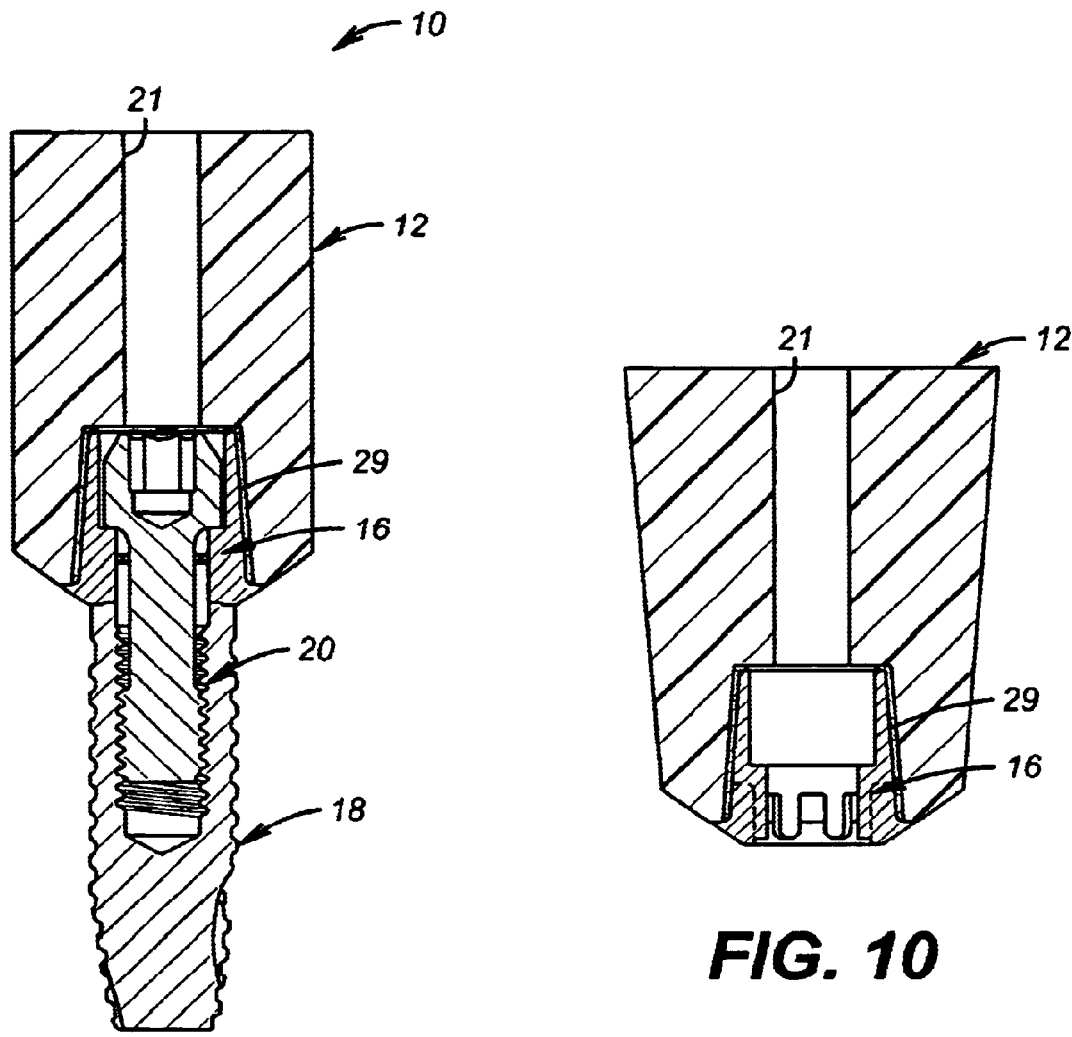
FIG. 9 is a cross-sectional side view illustrating another embodiment of a dental prosthetic assembly.
FIG. 10 is a cross-sectional view of an embodiment of a core with a tapered outside diameter.

FIGS. 9 and 10 show another embodiment of the present invention and in particular illustrate an alternative way to attach crown 12 to core 16. A layer of material 29 is provided between the crown and the core. This material is suitable for bonding the two components when the components are heated. This layer of material may be a heat activated adhesive or may be formed from precious metals, such as gold, silver, platinum, palladium, or alloys formed from these metals.

In the preferred embodiment, the core is fabricated from gold (or a gold alloy) and then gold (or a gold alloy) is used to bond the core and the crown. Gold is advantageous since it is both strong and biocompatible. Further, dental gold alloys are capable of withstanding higher temperatures than titanium.

Preferably, the gold is applied to the inner bore in the crown. The gold core and crown are then connected together, and heat is applied to bond them permanently together. The bonding may occur after an outer layer of porcelain is applied to the crown and subsequently heated or baked to bond the porcelain to the ceramic crown. This latter step often occurs since dental laboratories bake shades of porcelain onto the ceramic crown to match color of natural teeth. The heat during this operation melts or activates the layer of material 29. After the prosthesis is heated, the porcelain baked, and the crown and core bonded, the prosthesis is ready to be implanted into the jawbone of the patient. As shown in FIGS. 9 and 10, a hole 21 may be left in the crown to provide access to the screw 20.

Gold soldering or a brazing process can be used to join the core to the crown. A dental laboratory, for example, can add the soldering or brazing gold, or the gold can be supplied as a preform coating installed during the manufacturing stage. The preform coating can also be added using an electroplating process that metallizes the surface of the internal bore and bonds the crown and core.

Figure 11:
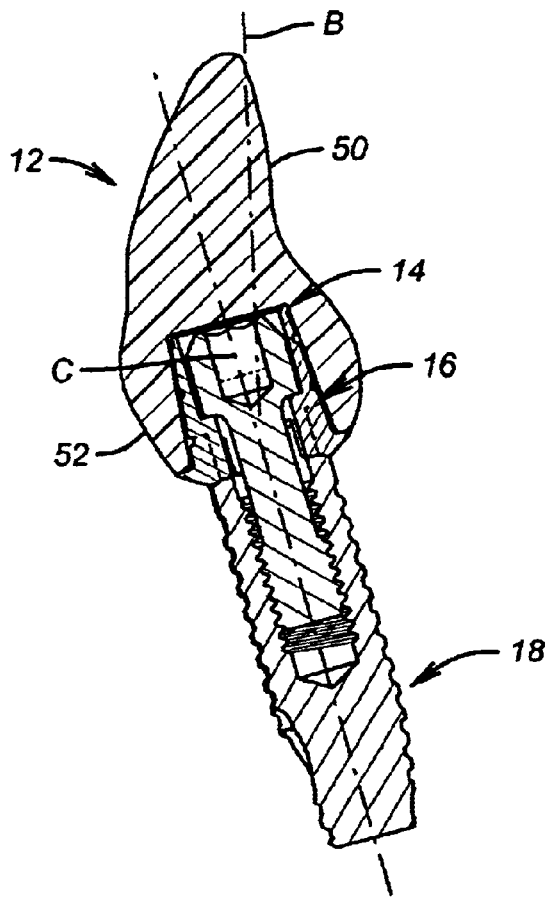
FIG. 11 is a cross-sectional side view showing an angled crown of the dental prosthetic assembly.
Figure 12:
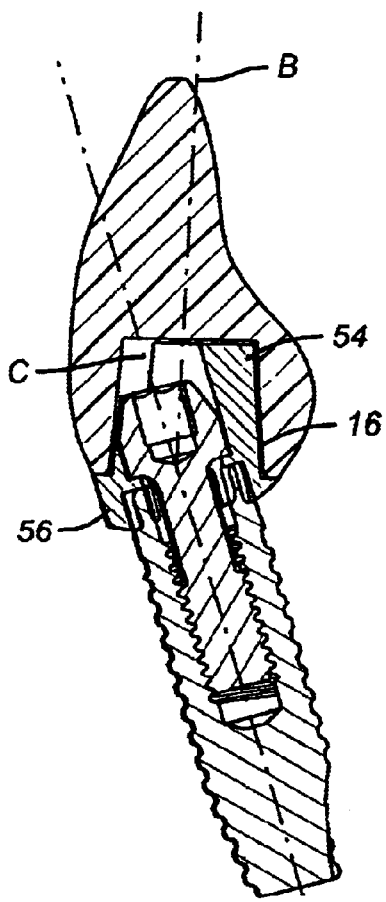
FIG. 12 is a cross-sectional side view showing another embodiment of an angled crown of the dental prosthetic assembly.

In another embodiment of the invention, the crown may be angled to provide proper alignment or angular correction of the prosthesis in the jawbone of the patient. FIGS. 11 and 12 show two different embodiments for angling the crown 12. In FIG. 11, a central axis C extends downwardly through the core 16 and anchor 18. An incisal axis B extends through the crown 12 and at an angle to axis C. As shown, crown 12 has two portions: a top coronal portion 50 and a bottom apical portion 52. The coronal portion 50 is canted with respect to central axis C to provide the noted angulation.

Looking now to FIG. 12, the core 16 has two portions: a top or upper portion 54 and a bottom or base portion 56. The upper portion 54 is angled or tilted relative to the base portion 56. Further, axis C and axis B show the relative angulation of the core.

Figure 13:
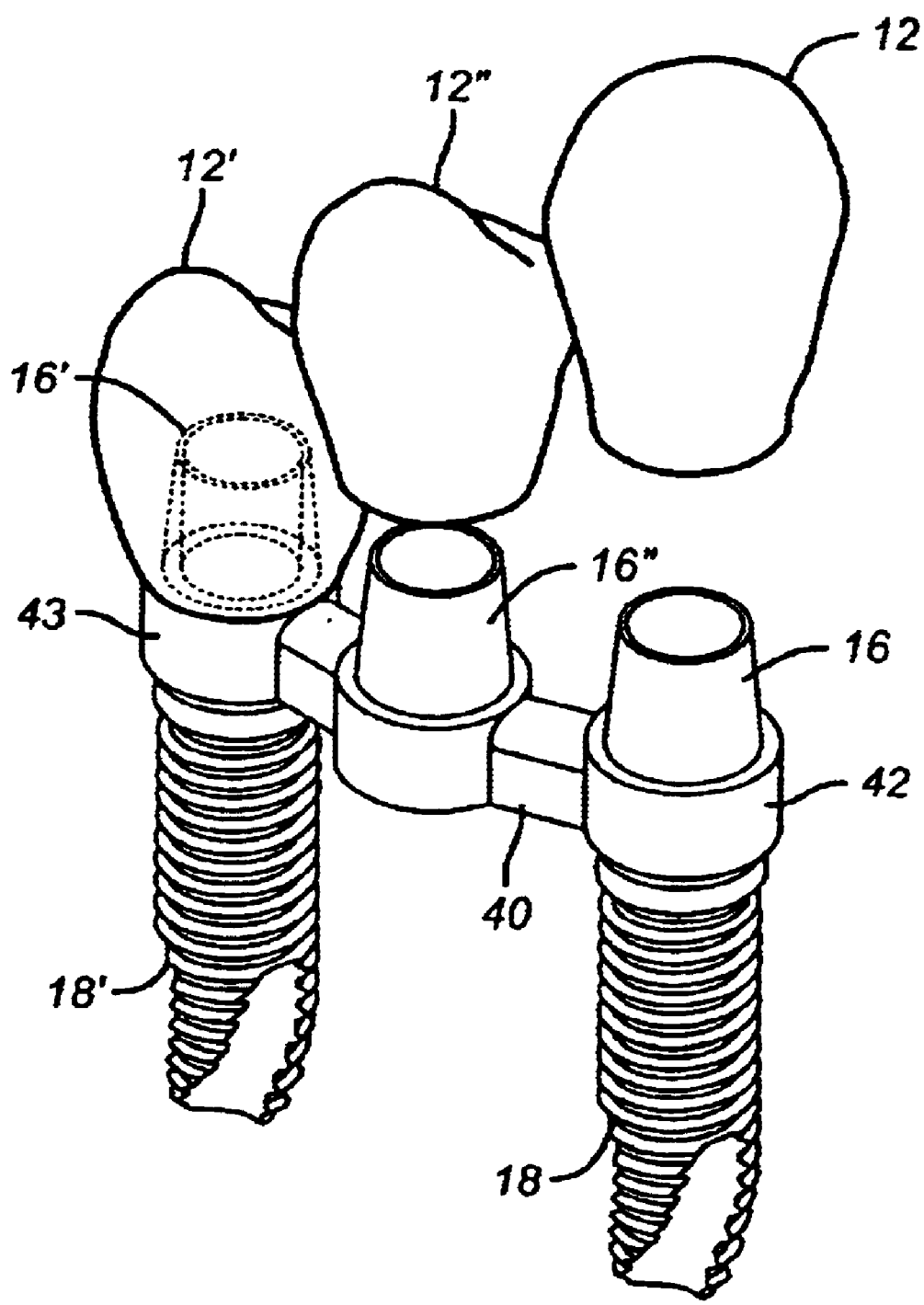
FIG. 13 is a three dimensional view illustrating an embodiment of a dental bridge with multiple near net crowns and cores.

If it is desired to restore multiple adjacent teeth, an interconnecting bar member 40, FIG. 13, may be used. For example, a pair of spaced apart anchors 18, 18' may be implanted in the jawbone. Each anchor 18, 18' includes a respective core 16, 16' attached thereto as discussed above. The bar 40 includes opposite terminal ends 42, 43 that are each attached to one of the anchors 18, 18', respectively. Bar 40 carries another, or mid-position core 16" which is positioned between the cores 16, 16' attached to the anchors 18, 18'. Thus, when the bar 40 is attached to the anchors 18, 18', the mid-position core 16" is aligned with the cores 16, 16' attached to the anchors 18, 18'. Crowns 12, 12', 12" can then be attached, via their core receiving bores, to a respective one of the cores 16, 16', 16" so that a multiple unit bridge is formed of near net tooth shaped crowns. The bar 40 can be formed using a variety of methods including a metal casting, or a ceramic pontic. Several methods including the application of an acrylic or porcelain to form a "ridge lap" can be used to hide the bar and create an aesthetic result.

Figure 14:
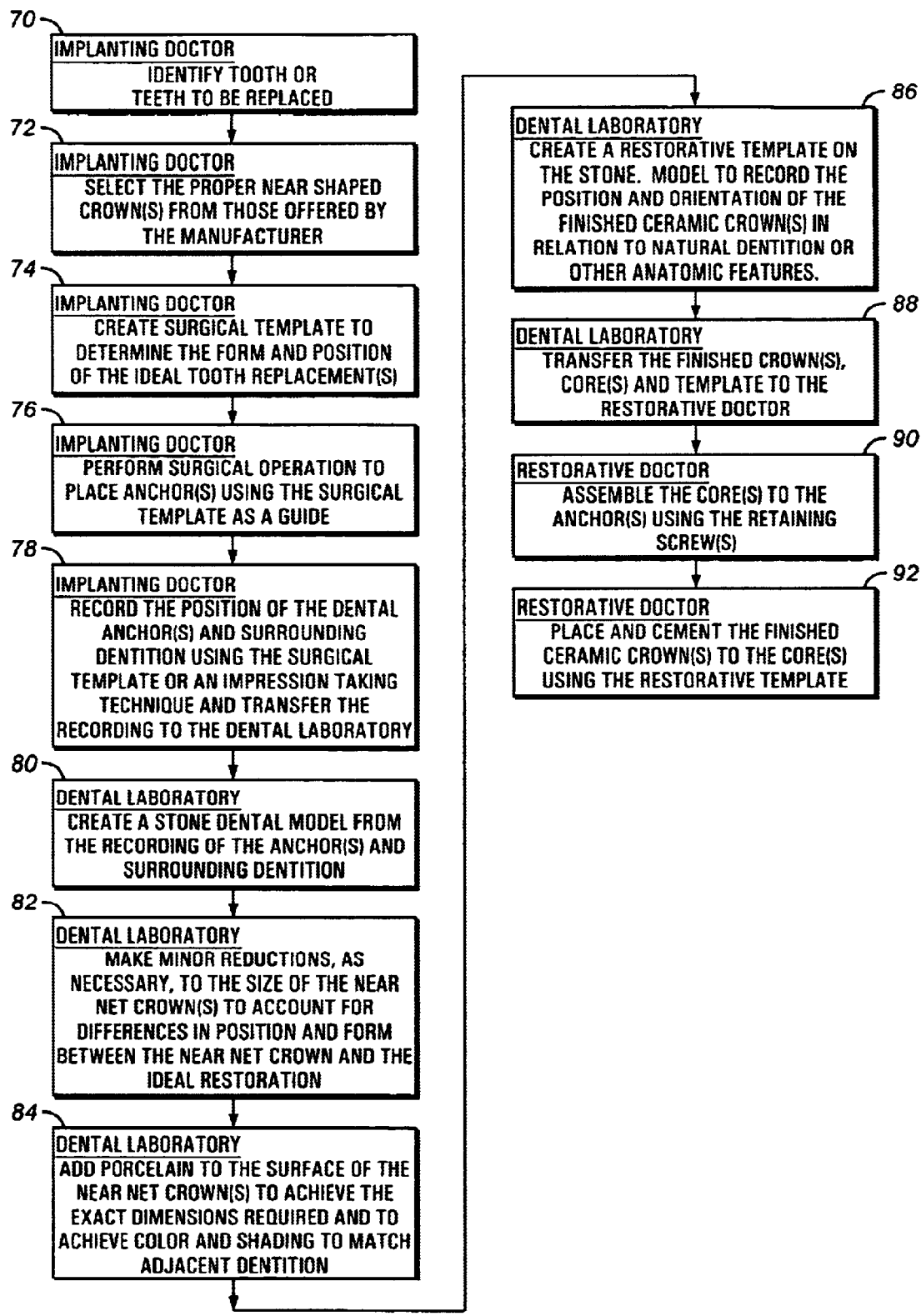
FIG. 14 is a flow diagram showing a method for utilizing the dental prosthetic system of the present invention.

FIG. 14 illustrates a method for utilizing a dental prosthesis of the present invention. The present invention will work with single and multiple restorations and extraction and edentulous sites. For illustration purposes, the method for a single-tooth restoration is discussed.

As shown in block 70, in the first step, the implanting doctor (i.e., dental implantologist) examines the patient and determines the tooth or teeth that need to be replaced. Per blocks 72 and 74, the next step is to create a surgical template. The template helps to determine the form and position of the tooth replacement. Based on the information from the template, the implanting doctor can then select the proper near net shaped ceramic crown, as shown in block 74. These near net crowns are manufactured to have a shape of a human natural tooth and then offered for sale to the clinician, laboratory, implanting doctor, or the like.

Next, per block 76, the doctor implants the anchor into the jawbone of the patient using the surgical template as a guide. The present invention will support various implants known to those skilled in the art. Next, per block 78, the doctor records the position of the dental anchor and surrounding dentition. An impression can be taken or the surgical template can be used to record these positions. Once the information is recorded, it is transferred to a dental laboratory.

As shown in block 80, the dental laboratory uses the recorded information to create a stone model of the anchor and surrounding dentition. At this point, as shown in block 82, minor corrections (such as a reduction) may be made to the shape of the near net crown. These corrections may be made, for example, to account for differences in position and form between the near net crown and an ideal prosthetic restoration. In the next step, block 84, the dental laboratory adds porcelain to the surface of the near net crown. The addition of the porcelain helps to achieve the exact dimensions required and helps to achieve the correct color and shading to match adjacent dentition.

In block 86, the laboratory creates a restorative template on the stone model to record the position and orientation of the finished ceramic crown in relation to natural dentition or other anatomical features. In block 88, the laboratory transfers the finished crowns, cores, and templates to the restorative doctor.

In block 90, the restorative doctor assembles the cores to the coronal end of the implants. A retaining screw may be used to connect a core to an implant. Lastly, in block 92, a finished ceramic crown is cemented on the end of the core. The restorative template is used to place the crown in the correct position and orientation.

Although illustrative embodiments have been shown and described, a wide range of modification, change, and substitution is contemplated in the foregoing disclosure without departing from the scope of the invention.

What is claimed is:

1. A dental implant prosthetic system, comprising:
   a dental implant having a coronal end with an internally threaded bore;
   a plurality of prosthetic teeth, each tooth adapted to connect to the coronal end of the same implant and each tooth having a metallic core and a ceramic crown, wherein the core has an outer surface and an internal bore, and wherein the crown is attached to the outer surface of the core and the crown is prefabricated to have an anatomical shape and size of a natural human tooth, wherein the plurality of prosthetic teeth are provided with ceramic crowns having a plurality of different shapes and wherein at least a single tooth is selected from the plurality of teeth and attached to the coronal end of the implant; and
   a screw adapted to seat in the internal bore of the core and connect the tooth to the implant.

2. The dental prosthetic system of claim 1 wherein at least one ceramic crown has a shape selected from the group consisting of incisor, canine, premolar, and molar.

3. The dental implant prosthetic system in claim 2 wherein the crown is made slightly smaller than a natural crown.

4. The dental implant prosthetic system of claim 3 wherein the crown has a diameter of 0.5 mm to 1.5 mm smaller than a diameter of the natural crown.

5. The dental implant prosthetic system in claim 2 wherein the ceramic of the crown is baked and hardened.

6. The dental implant prosthetic system in claim 5 wherein the core is fabricated from titanium, titanium alloy, or gold alloy.

7. The dental implant prosthetic system in claim 2 wherein the crown is fabricated from aluminum oxide, zirconium oxide, a composite of aluminum oxide and zirconium oxide, or a combination of ceramic and polymeric materials.

8. The dental implant prosthetic system in claim 7 wherein the crown has a natural color of human teeth.

9. The dental implant prosthetic system in claim 8 wherein the crown has an external layer of porcelain.

10. A method for installing a dental prosthetic tooth onto a dental implant in the jawbone of human, comprising the steps of:
    identifying a replacement site in the jawbone to receive a prosthetic tooth; providing a dental implant;
    providing a plurality of prosthetic teeth having a plurality of different sizes, each prosthetic tooth adapted to connect to a coronal end of the implant and each prosthetic tooth having a ceramic crown connected to an internal metallic core, wherein the crown manufactured to have an anatomical shape and size of a natural human tooth;
    recording a size and shape of the replacement site;
    selecting one of the manufactured prosthetic teeth that has a size and shape similar to the size and shape of the replacement site;
    implanting the dental implant into the jawbone of the patient;
    recording the position of the dental implant in the jawbone; and
    connecting the prosthetic tooth to the dental implant.

11. The method of claim 10 wherein the step of selecting one of the manufactured prosthetic teeth further includes selecting from one of a prefabricated crown with a shape and size of a human incisor, canine, premolar, or molar.

12. The method of claim 11 further including the step of correcting the size or shape of the prosthetic tooth to match the size and shape of the replacement site.

13. The method of claim 12 wherein the step of correcting the prosthetic tooth further includes the step of adding porcelain to a surface of the prosthetic tooth.

14. A dental implant prosthetic system, comprising:
    a dental implant having a coronal end; and
    a plurality of prosthetic teeth, each tooth adapted to connect to the coronal end of the same implant and each tooth having a metallic core and a ceramic crown, wherein the core has an outer surface and an internal bore, and wherein the crown is attached to the outer surface of the core and the crown is prefabricated to have an anatomical shape and size of a natural human tooth, wherein the plurality of prosthetic teeth are provided with ceramic crowns having a plurality of different shapes and wherein at least a single tooth is selected from the plurality of teeth and attached to the coronal end of the implant.

15. The dental implant prosthetic system of claim 14 wherein at least one ceramic crown has a shape selected from the group consisting of incisor, canine, premolar, and molar.

16. The dental implant prosthetic system of claim 15 wherein the crown is manufactured to have a size that is slightly smaller than a natural tooth.

17. The dental implant prosthetic system of claim 16 wherein the crown is adapted to receive a layer of porcelain, and wherein the crown has a natural color of human teeth.

* * * * *